United States Patent [19]

Bastart et al.

[11] Patent Number: 5,750,738
[45] Date of Patent: May 12, 1998

[54] PROCESS FOR THE PREPARATION OF 7-HYDROXYTAXANES

[75] Inventors: Jean-Pierre Bastart, Lesigny; Jean-Dominique Boursat, Vincennes; Alain Commercon, Vitry-Sur-Seine; Jean-Pierre Leconte, Brunoy, all of France

[73] Assignee: Rhone-Poulenc Rorer S.A., France

[21] Appl. No.: 722,106

[22] PCT Filed: Apr. 3, 1995

[86] PCT No.: PCT/FR95/00420

§ 371 Date: Oct. 3, 1996

§ 102(e) Date: Oct. 3, 1996

[87] PCT Pub. No.: WO95/26961

PCT Pub. Date: Oct. 12, 1995

[30] Foreign Application Priority Data

Apr. 5, 1994 [FR] France ..................... 9403980

[51] Int. Cl.$^6$ ..................... C07D 305/14
[52] U.S. Cl. ..................... 549/510; 549/511
[58] Field of Search ..................... 549/510, 511

[56] References Cited

U.S. PATENT DOCUMENTS 5,578,739 11/1996 Hittinger ..................... 549/510

*Primary Examiner*—Ba K. Trinh
*Attorney, Agent, or Firm*—Finnegan, Henderson, Farabow, Garrett & Dunner, L.L.P.

[57] ABSTRACT

This invention relates to a process for the preparation of 7-hydroxy taxanes of general formula (I) from 7-trialkylsilyl taxanes of general formula (II), wherein $R_1$ is hydrogen, alkoxy, acyloxy, or alkoxyacetoxy, and Z is a hydrogen atom or a radical of general formula (III), wherein $R_2$ is an optionally substituted benzyl radical or an $R'_2$—O—CO— radical wherein $R'_2$ is an alkyl, alkenyl, alkynyl, cycloalkyl, cycloalkenyl, bicycloalkyl, optionally substituted phenyl or heterocyclyl radical. $R_3$ is an aromatic alkyl, alkenyl, alkynyl, cycloalyl, phenyl, naphthyl or heterocyclyl radical and either $R_4$ is a hydrogen atom and $R_5$ is a hydroxyl function protecting group, or $R_4$ and $R_5$ together form a saturated 5- or 6-membered heterocyclic ring. In general formula (II), each R, which are the same or different, is an alkyl radical optionally substituted by a phenyl radical.

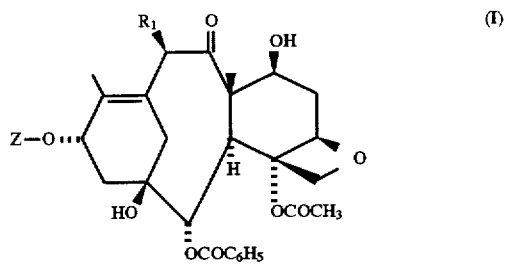

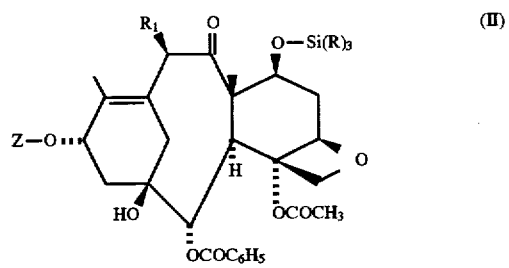

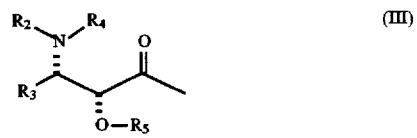

5 Claims, No Drawings

PROCESS FOR THE PREPARATION OF 7-HYDROXYTAXANES

This application is a 371 of PCT/FR95/00420 dated Apr. 3, 1995.

The present invention relates to a process for the preparation of 7-hydroxytaxanes of general formula:

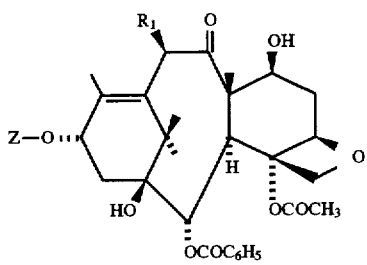

starting with a product of general formula:

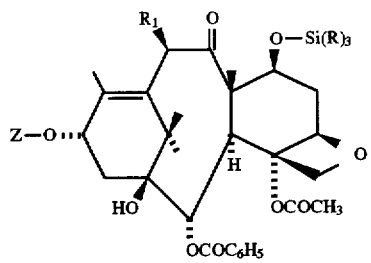

In the general formulae (I) and (II): $R_1$ represents a hydrogen atom or an alkoxy radical containing 1 to 4 carbon atoms, an alkoxyacetoxy radical in which the alkyl part contains 1 to 4 carbon atoms or an alkanoyloxy radical containing 1 to 4 carbon atoms, and Z represents a hydrogen atom or a radical of general formula:

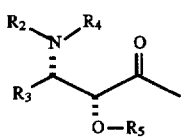

in which:

$R_2$ represents a benzoyl radical which is optionally substituted with one or more atoms or radicals, which may be identical or different, chosen from halogen atoms and alkyl radicals containing 1 to 4 carbon atoms, alkoxy radicals containing 1 to 4 carbon atoms and trifluoromethyl radicals, or a radical $R'_2$—O—CO— in which $R'_2$ represents an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms, or a bicycloalkyl radical containing 7 to 10 carbon atoms, these radicals optionally being substituted with one or more substituents chosen from halogen atoms and hydroxyl radicals, alkoxy radicals containing 1 to 4 carbon atoms, dialkylamino radicals in which each alkyl part contains 1 to 4 carbon atoms, piperidino or morpholino radicals, 1-piperazinyl radicals (optionally substituted at –4 with an alkyl radical containing 1 to 4 carbon atoms or with a phenylalkyl radical in which the alkyl part contains 1 to 4 carbon atoms), cycloalkyl radicals containing 3 to 6 carbon atoms, cycloalkenyl radicals containing 4 to 6 carbon atoms, phenyl radicals (optionally substituted with one or more atoms or radicals chosen from halogen atoms and alkyl radicals containing 1 to 4 carbon atoms or alkoxy radicals containing 1 to 4 carbon atoms), cyano or carboxyl radicals or alkoxycarbonyl radicals in which the alkyl part contains 1 to 4 carbon atoms, a phenyl or α- or β-naphthyl radical which is optionally substituted with one or more atoms or radicals chosen from halogen atoms and alkyl radicals containing 1 to 4 carbon atoms or alkoxy radicals containing 1 to 4 carbon atoms or a 5-membered aromatic heterocyclic radical preferably chosen from furyl and thienyl radicals, or a saturated nitrogen-containing heterocyclic radical containing 4 to 6 carbon atoms which is optionally substituted with one or more alkyl radicals containing 1 to 4 carbon atoms, and $R_3$ represents a straight or branched alkyl radical containing 1 to 8 carbon atoms, a straight or branched alkenyl radical containing 2 to 8 carbon atoms, a straight or branched alkynyl radical containing 2 to 8 carbon atoms, a cycloalkyl radical containing 3 to 6 carbon atoms, a phenyl or α- or β-naphthyl radical which is optionally substituted with one or more atoms or radicals chosen from halogen atoms and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more hetero atoms, which may be identical or different, chosen from nitrogen, oxygen or sulphur atoms and optionally substituted with one or more substituents, which may be identical or different, chosen from halogen atoms and alkyl, aryl, amino, alkylamino, dialkylamino, alkoxycarbonylamino, acyl, arylcarbonyl, cyano, carboxyl, carbamoyl, alkylcarbamoyl, dialkylcarbamoyl or alkoxycarbonyl radicals, it being understood that, in the substituents for the phenyl, α- or β-naphthyl radicals and aromatic heterocyclic radicals, the alkyl radicals and the alkyl portions of the other radicals contain 1 to 4 carbon atoms and that the alkenyl and alkynyl radicals contain 2 to 8 carbon atoms and that the aryl radicals are phenyl or α- or β-naphthyl radicals, and either $R_4$ represents a hydrogen atom and $R_5$ represents a hydrogen atom or a protecting group for the hydroxyl function, or $R_4$ and $R_5$ together form a 5- or 6-membered saturated heterocycle.

In the general formula (II), the symbols R, which may be identical or different, each represent a straight or branched alkyl radical containing 1 to 4 carbon atoms which is optionally substituted with a phenyl radical.

More particularly, the present invention relates to a process for the preparation of the 7-hydroxytaxanes of general formula (I) in which $R_1$ represents a hydrogen atom or an alkoxy radical containing 1 to 4 carbon atoms, an acyloxy radical containing 1 to 4 carbon atoms or an alkoxyacetoxy radical in which the alkyl part contains 1 to 4 carbon atoms, Z represents a hydrogen atom or a radical of general formula (III) in which $R_2$ represents a benzoyl radical or a radical $R'_2$—O—CO— in which $R'_2$ represents a tert-butyl radical and $R_3$ represents an alkyl radical containing 1 to 6 carbon atoms, an alkenyl radical containing 2 to 6 carbon atoms, a cycloalkyl radical containing 3 to 6 carbon atoms, a phenyl radical which is optionally substituted with one or more atoms or radicals, which may be identical or different, chosen from halogen atoms (fluorine or chlorine) and alkyl (methyl), alkoxy (methoxy), dialkylamino (dimethylamino), acylamino (acetylamino), alkoxycarbonylamino (tert-butoxycarbonylamino) or trifluoromethyl radicals or a 2- or 3-furyl, 2- or 3-thienyl or 2-, 4- or 5-thiazolyl radical, and, either $R_4$ represents a hydrogen atom and $R_5$ represents a hydrogen atom or a methoxymethyl, 1-ethoxyethyl, benzyloxymethyl or tetrahydropyranyl radical, or $R_4$ and $R_5$ together form an oxazolidine ring which is mono-substituted or gem -disubstituted in position -2.

Even more particularly, the present invention relates to the preparation of the 7-hydroxytaxanes of general formula (I) in which $R_1$ represents an acetyloxy radical, Z represents a hydrogen atom or a radical of general formula (III) in which $R_2$ represents a benzoyl radical or a radical $R'_2$—O—CO— in which $R'_2$ represents a tert-butyl radical, $R_3$ represents an isobutyl, isobutenyl, cyclohexyl, phenyl, 2-furyl, 3-furyl, 2-thienyl, 3-thienyl, 2-thiazolyl, 4-thiazolyl or 5-thiazolyl radical and $R_4$ and $R_5$ together form an oxazolidine ring which is substituted in position 2 with a 4-methoxyphenyl radical.

According to the invention, the products of general formula (I) are obtained by treating a product of general formula (II) with trifluoroacetic acid in a basic organic solvent, such as pyridine which is optionally substituted with one or more alkyl radicals containing 1 to 4 carbon atoms, optionally combined with an inert organic solvent, such as acetonitrile, at a temperature between 20° and 80° C. It is particularly advantageous to use a product of general formula (II) in which the symbols R each represent an ethyl radical.

In particular, by working under the conditions of the process according to the invention, the replacement of the trialkylsilyloxy radical with a hydroxyl radical is carried out without touching the rest of the molecule and in particular, when Z represents a radical of general formula (III), without touching the protecting group represented by $R_5$ or without touching the ring formed by $R_4$ and $R_5$.

The products of general formula (I) are particularly useful for preparing the taxoids corresponding to the general formulae:

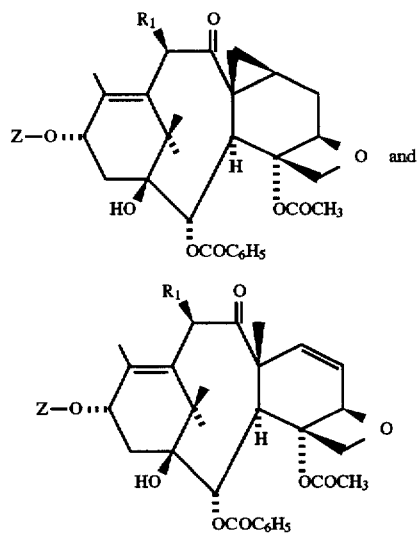

in which $R_1$ and Z are defined as above, by passing via an intermediate product of general formula:

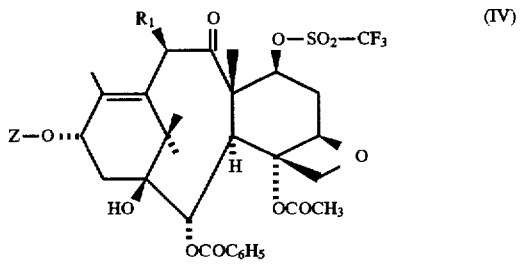

in which $R_1$ and Z are defined as above.

The products of general formula (IV) may be obtained by the action of an alkali metal halide (sodium chloride, sodium iodide, or potassium fluoride) or an alkali metal azide (sodium azide) or a quaternary ammonium salt or an alkali metal phosphate on a product of general formula (VI), in an organic solvent chosen from ethers (tetrahydrofuran, diisopropyl ether or methyl tert-butyl ether) and nitrites (acetonitrile) taken alone or as a mixture, at a temperature between 20° C. and the boiling point of the reaction mixture.

The products of general formula (V) may be obtained by treating a product of general formula (VI) with a base chosen from basic organic solvents such as pyridine, pyridines substituted with one or more alkyl radicals containing 1 to 4 carbon atoms and quinoline, at a temperature between 30° and 80° C.

The products of general formula (VI) may be obtained by the action of a trifluoromethanesulphonic acid derivative such as the anhydride, the acid fluoride or the N-phenyltrifluoromethanesulphonimide, working in an inert organic solvent (aromatic hydrocarbons or optionally halogenated aliphatic hydrocarbons), in the presence of an organic base such as an aliphatic tertiary amine (triethylamine) or pyridine, at a temperature between −50° and +20° C.

The products of general formulae (IV) and (V), in which Z represents a radical of general formula (III) in which, $R_2$ and $R_3$ being defined as above, $R_4$ and $R_5$ each represent a hydrogen atom, exhibit noteworthy anti-cancer and antileukaemia properties.

The examples which follow illustrate the present invention.

EXAMPLE 1

To a solution of 25 g of 4α-,10β-diacetoxy -2α-benzoyloxy-5β,20-epoxy-7β-triethylsilyloxy-9-oxo-1β-hydroxy-11-taxen-13α-yl (2R,4S,5R)-3-tert-butoxy -carbonyl-2-(4-methoxyphenyl)-4-phenyl-5-oxazolidine -carboxylate in 125 cm³ of acetonitrile and 111 cm³ of pyridine, cooled to 5° C., are added 103.6 g of trifluoroacetic acid over 45 minutes. The mixture is stirred for 15 hours at 50° C. A further 28 cm³ of pyridine and 25.9 g of trifluoroacetic acid are added and the mixture is stirred for 10 hours at 50° C. A further 28 cm³ of pyridine and 25.9 g of trifluoroacetic acid are added and the mixture is stirred for 15 hours at 50° C. The reaction mixture is cooled to 20° C. and is then poured into 4 liters of ice-water. The suspension is filtered. The precipitate is washed with 10 times 200 cm³ of distilled water, is air-dried and is then washed with 140 cm³ of isopropyl ether, drained and finally washed with twice 46 cm³ of isopropyl ether. 21.7 g of 4α,10β-diacetoxy- 2α-benzoyloxy-5β,20-epoxy-1β,7β-dihydroxy-9-oxo-11-taxen-13α-yl (2R,4S,5R)-3-tert-butoxycarbonyl-2-(4-methoxyphenyl)-4-phenyl-5-oxazolidinecarboxylate are thus obtained in a yield of 97%, the characteristics of which are as follows:

melting point: 178° C.

proton nuclear magnetic resonance spectrum: (400 MHz; $CDCl_3$; temperature of 323° K, δ in ppm): 1.07 [s, 9H:

C(CH₃)₃]; 1.12 (s, 3H: CH₃); 1.27 (s. 3H: CH₃); 1.58 (s. 3H: CH₃) ; 1.66 (s, 3H: CH₃); 1.85 and 2.50 (2 mt, 1H each: CH₂ at 6); 1.86 (s, 3H: COCH₃); 2.13 and 2.21 (2 dd, J=16 and 9 Hz, 1H each: CH₂ at 14); 2.24 (s, 3H: COCH₃); 3.72 (d, J=7 Hz; 1H: H at 3); 3.82 (s, 3H: OCH₃); 4.12 and 4.24 (2d, J=8 Hz, 1H each: CH₂ at 20); 4.38 (dd, J=11 and 6 Hz, 1H: H 7); 4.58 (d, J=5.5 Hz, 1H: H 2); 4.89 (dd, J=10 and 3.5 Hz, 1H: H at 5); 5.43 (d, J=5.5 Hz, 1H: H at 3); 5.63 (d, J=7 Hz, 1H: H at 2); 6.14 (t, J=9 Hz, 1H: H at 13); 6.22 (s, 1H: H 10); 6.38 (broad s, 1H: H 5); 6.93 (d, J=8.5 Hz, 2H: C₆H₅ H ortho to the OCH₃); from 7.30 to 7.50 (mt, 7H: C₆H₅ at 3 and C6H₅ meta to the OCH₃); 7.48 (t, J=8.5 Hz, 2H: —OCOC₆H₅ at meta position); 7.62 (t, J=8.5 Hz, 1H: —OCOC₆H₅ H at para position); 8.03 (d, J=8.5 Hz, 2H: —OCOC₆H₅ H at ortho position).

4α,10β-Diacetoxy-2α-benzoyloxy-5β,20-epoxy-7β-triethylsilyloxy-9-oxo-1β-hydroxy-11-taxen-13α-yl (2R,4S,5R)-3-tert-butoxycarbonyl-2-(4-methoxyphenyl)-4-phenyl-5-oxazolidinecarboxylate may be prepared in the following way:

To a solution of 147 g of 7-triethylsilylbaccatin III and 100 g of 3-tert-butoxycarbonyl-2-(4-methoxyphenyl)-4-phenyl-5-oxazolidinecarboxylic acid in 720 cm³ of ethyl acetate, cooled to a temperature in the region of 5° C., are successively added 64.7 g of 1,3-di-cyclohexylcarbodiimide and 5.6 g of 4-dimethylaminopyridine.

The suspension thus obtained is stirred for 4 hours at 20° C. and then filtered. The filtrate is washed with twice 500 cm₃ of half-saturated aqueous sodium hydrogen carbonate solution, twice 500 cm³ of distilled water and twice 500 cm³ of saturated aqueous sodium chloride solution.

The organic phase is dried over magnesium sulphate. After filtration and concentration to dryness under reduced pressure, the product obtained is crystallized from 750 cm³ of methyl tert-butyl ether, and 126.9 g of 4α,10β-diacetoxy-2α-benzoyloxy-5β,20-epoxy-7β-triethylsilyloxy-9-oxo-1β-hydroxy-11-taxen-13α-yl(2R,4S,5R)-3-tert-butoxycarbonyl-2-(4-methoxy -phenyl)-4-phenyl-5-oxazolidinecarboxylate are obtained, the characteristics of which are as follows:

melting point: 174° C.

proton nuclear magnetic resonance spectrum: (400 MHz; CDCl₃;δin ppm): 0.58 (mt, 6H: CH₂); 0.92 (t, J=7.5 Hz, 9H: CH₃); 1.02 (s, 3H: CH₃); 1.18 (s, 3H: CH₃); 1.68 (s, 3H: CH₃); 1.75 (broad s, 1H: OH at 1); 1.87 and 2.53 (2 mt, 1H each: CH₂ at 6); 2.18 (s, 6H: CH₃ and COCH₃); 2.27 (mt, 2H: CH₂ at 14); 2.28 (s, 3H: COCH₃); 2.47 (broad s, 1H: OH at 13); 3.88 (d, J=7 Hz, 1H: H at 3); 4.13 and 4.30 (2d, J=8.5 Hz, 1H each: CH₂ at 20); 4.50 (dd, J=11 and 7 Hz, 1H: H 7); 4.81 (mt, 1H: H at 13); 4.95 (broad d, J=10 Hz, 1H: H at 5); 5.63 (d, J=7 Hz, 1H: H 2); 6.46 (s, 1H: H at 10); 7.46 (t, J=8.5 Hz, 2H: —OCOC₆H₅ H at meta position); 7.60 (t, J =8.5 Hz, 1H: —OCOC₆H₅ H at para position); 8.10 (d, J=8.5 Hz, 2H: OCOC₆H₅ H at ortho position).

7-Triethylsilylbaccatin III may be prepared in the following way:

To a solution of 293.9 g of 10-deacetylbaccatin baccatin III in 2.7 liters of pyridine are added 182 g of triethylsilyl chloride over 1 hour 20 minutes. The solution obtained is stirred for 40 hours at 5° C. 360 g of acetic anhydride are then added while maintaining the temperature at 5° C. The suspension obtained is stirred for 48 hours at 20° C. and then poured into 40 liter of ice-water. The precipitate obtained is isolated by filtration and then washed with 8 times 2 liters of water and finally dissolved in 3 liters of ethyl acetate. The organic phase is dried over magnesium sulphate. After filtration and concentration under reduced pressure, the product obtained is crystallized from isopropyl ether. 7-Triethylsilylbaccatin III is thus obtained in a yield of 77%, the characteristics of which are as follows:

melting point: 254° C.

proton nuclear magnetic resonance spectrum: (400 MHz; CDCl₃,δin ppm); 0.58 (mt, 6H: CH₂ ethyl); 0.92 (t, J=7.5 Hz, 9H: CH₃ ethyl); 1.02 (s, 3H: CH₃); 1.18 (s, 3H: CH₃); 1.68 (s, 3H: CH₃); 1.75 (broad s, 1H: OH at 1); 1.87 and 2.53 (2 mt, 1H each: CH₂ at 6); 2.18 (s, 6H: CH₃ and COCH₃); 2.27 (mt, 2H: CH₂ at 14); 2.28 (s, 3H: COCH₃); 2.47 (broad s, 1H: OH at 13); 3.88 (d, J=7 Hz, 1H: H 3); 4.13 and 4.30 (2d, J=8.5 Hz, 1H each: CH₂ at 20); 4.50 (dd, J=11 and 7 Hz, 1H: H at 7); 4.81 (mt, 1H: H at 13); 4.95 (broad d, J=10 Hz, 1H: H at 5); 5.63 (d, J=7 Hz, 1H: H 2); 6.46 (s, 1H: H at 10); 7.46 (t, J=8.5 Hz, 2H: —OCOC₆H₅ H at meta position); 7.60 (t, J=8.5 Hz, 1H: —OCOC₆H₅ H at para position); 8.10 (d, J=8.5 Hz, 2H: —OCOC₆H₅ H at ortho position).

EXAMPLE 2

To a solution of 350 mg of 7-triethylsilylbaccatin III in 3 cm³ of acetonitrile and 2.4 cm³ of pyridine are added 2.3 g of trifluoroacetic acid. The mixture is stirred for 48 hours at 50° C. After cooling, the reaction mixture is taken up in 50 cm³ of methylene chloride, washed with twice 5 cm³ of distilled water, 10 cm³ of 1N hydrochloric acid and twice 5 cm³ of distilled water, and dried over magnesium sulphate. After filtration and concentration to dryness under reduced pressure, 330 mg of a product are obtained, which product is purified by chromatography on 30 g of silica contained in a column 2 cm in diameter, eluting with a methylene chloride/methanol mixture (99/1 by volume). The first 300 cm³ eluted are discarded. The next 275 cm³ provide, after concentration to dryness, 235 mg of baccatin III in the form of a white foam. The yield is 83%.

I claim:

1. Process for the preparation of 7-hydroxytaxanes of general formula:

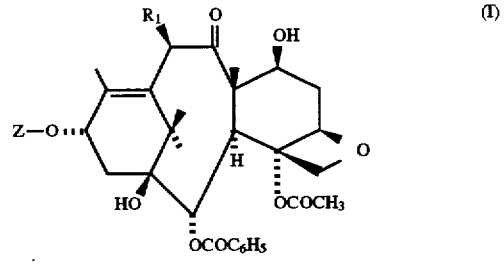

in which

R₁ represents a hydrogen atom or an alkoxy radical containing 1 to 4 carbon atoms, an alkoxyacetoxy radical in which the alkyl part contains 1 to 4 carbon atoms or an alkanoyloxy radical containing 1 to 4 carbon atoms, and Z represents a hydrogen atom or a radical of general formula:

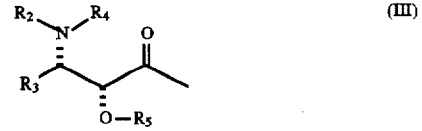

in which:

R₂ represents a benzoyl radical which is optionally substituted with one or more atoms or radicals, which may be identical or different, chosen from halogen atoms and alkyl radicals containing 1 to 4 carbon atoms, alkoxy radicals containing 1 to 4 carbon atoms and trifluoromethyl radicals, or a radical R'$_2$—O—CO— in which R'$_2$ represents represents an alkyl radical containing 1 to 8 carbon atoms, an alkenyl radical containing 2 t o 8 carbon atoms, an alkynyl radical containing 3 to 8 carbon atoms, a cycloalkyl radical containing 3 to 6 carbon atoms, a cycloalkenyl radical containing 4 to 6 carbon atoms, or a bicycloalkyl radical containing 7 to 10 carbon atoms, these radicals optionally being substituted with one or more substituents chosen from halogen atoms and hydroxyl radicals, alkoxy radicals containing 1 to 4 carbon atoms, dialkylamino radicals in which each alkyl part contains 1 to 4 carbon atoms, piperidino or morpholino radicals, 1-piperazinyl radicals (optionally substituted at −4 with an alkyl radical containing 1 to 4 carbon atoms or with a phenylalkyl radical in which the alkyl part contains 1 to 4 carbon atoms), cycloalkyl radicals containing 3 to 6 carbon atoms, cycloalkenyl radicals containing 4 to 6 carbon atoms, phenyl radicals (optionally substituted with one or more atoms or radicals chosen from halogen atoms and alkyl radicals containing 1 to 4 carbon atoms or alkoxy radicals containing 1 to 4 carbon atoms, cyano or carboxyl radicals or alkoxycarbonyl radicals in which the alkyl part contains 1 to 4 carbon atoms, a phenyl or α- or β-naphthyl radical which is optionally substituted with one or more atoms or radicals chosen from halogen atoms and alkyl radicals containing 1 to 4 carbon atoms or alkoxy radicals containing 1 to 4 carbon atoms or a 5-membered aromatic heterocyclic radical preferably chosen from furyl and thienyl radicals, or a saturated nitrogen-containing heterocyclic radical containing 4 to 6 carbon atoms which is optionally substituted with one or more alkyl radicals containing 1 to 4 carbon atoms, and R$_3$ represents a straight or branched alkyl radical containing 1 to 8 carbon atoms, a straight or branched alkenyl radical containing 2 to 8 carbon atoms, a straight or branched alkynyl radical containing 2 to 8 carbon atoms, a cycloalkyl radical containing 3 to 6 carbon atoms, a phenyl or α- or β-naphthyl radical which is optionally substituted with one or more atoms or radicals chosen from halogen atoms and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more hetero atoms, which may be identical or different, chosen from nitrogen, oxygen or sulphur atoms and optionally substituted with one or more substituents, which may be identical or different, chosen from halogen atoms and alkyl, aryl, amino, alkylamino, dialkylamino, alkoxycarbonylamino, acyl, arylcarbonyl, cyano, carboxyl, carbamoyl, alkylcarbamoyl, dialkylcarbamoyl or alkoxycarbonyl radicals, it being understood that, in the substituents for the phenyl, α- or β-naphthyl radicals and aromatic heterocyclic radicals, the alkyl radicals and the alkyl portions of the other radicals contain 1 to 4 carbon atoms and that the alkenyl and alkynyl radicals contain 2 to 8 carbon atoms and that the aryl radicals are phenyl or α- or β-naphthyl radicals, and either R$_4$ represents a hydrogen atom and R$_5$ represents a hydrogen atom or a protecting group for the hydroxyl function, or R$_4$ and R$_5$ together form a 5- or 6-membered saturated heterocycle, characterized in that a a product of general formula:

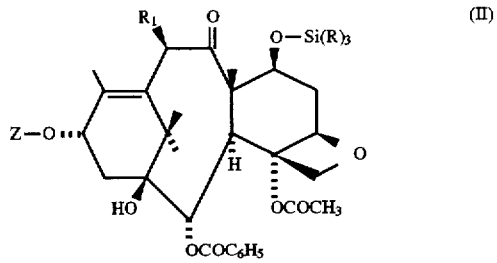

in which R$_1$ and Z are as defined above and the symbols R, which may be identical or different, each represent a straight or branched alkyl radical containing 1 to 4 carbon atoms which is optionally substituted with a phenyl radical, in converted to the formula (I) compound.

2. Process according to claim 1, characterized in that the basic-organic solvent is chosen from pyridine and pyridines substituted with one or more alkyl radicals containing 1 to 4 carbon atoms.

3. Process according to either of claims 1 and 2, characterized in that the process is performed at a temperature between 20° and 80° C.

4. Process according to one of claims 1 to 3 for the preparation of a product of general formula (I) in which R$_1$ represents a hydrogen atom or an alkoxy radical containing 1 to 4 carbon atoms, an acyloxy radical containing 1 to 4 carbon atoms or an alkoxyacetoxy radical in which the alkyl part contains 1 to 4 carbon atoms, Z represents a hydrogen atom or a radical of general formula (III) in which R$_2$ represents a benzoyl radical or a radical R'$_2$—O—CO— in which R'$_2$ represents a tert-butyl radical and R$_3$ represents an alkyl radical containing 1 to 6 carbon atoms, an alkenyl radical containing 2 to 6 carbon atoms, a cycloalkyl radical containing 3 to 6 carbon atoms, a phenyl radical which is optionally substituted with one or more atoms or radicals, which may be identical or different, chosen from halogen atoms (fluorine or chlorine) and alkyl (methyl), alkoxy (methoxy), dialkylamino (dimethylamino), acylamino (acetylamino), alkoxycarbonylamino (tert-butoxycarbonylamino) or trifluoromethyl radicals or a 2- or 3-furyl, 2- or 3-thienyl or 2-, 4- or 5-thiazolyl radical, and, either R$_4$ represents a hydrogen atom and R$_5$ represents a hydrogen atom or a methoxymethyl, 1-ethoxyethyl, benzyloxymethyl or tetrahydropyranyl radical, or R$_4$ and R$_5$ together form an oxazolidine ring which is mono-substituted or gem-disubstituted in position −2.

5. Process according to one of claims 1 to 3 for the preparation of a product of general formula (I) in which R$_1$ represents an acetyloxy radical, Z represents a hydrogen atom or a radical of general formula (III) in which R$_2$ represents a benzoyl radical or a radical R'$_2$—O—CO— in which R'$_2$ represents a tert-butyl radical, R$_3$ represents an isobutyl, isobutenyl, cyclohexyl, phenyl, 2-furyl, 3-furyl, 2-thienyl, 3-thienyl, 2-thiazolyl, 4-thiazolyl or 5-thiazolyl radical and R$_4$ and R$_5$ together form an oxazolidine ring which is substituted in position 2 with a 4-methoxy-phenyl radical.

* * * * *

UNITED STATES PATENT AND TRADEMARK OFFICE
CERTIFICATE OF CORRECTION

PATENT NO. : 5,750,738
DATED : May 12, 1998
INVENTOR(S) : Jean-Pierre BASTART et al.

It is certified that error appears in the above-identified patent and that said Letters Patent is hereby corrected as shown below:

On Title Page, Item [75], in the Inventors, line 2, "Boursat" should read --Bourzat--; and line 3, "Commercon" should read --Commerçon--.

Claim 1, column 7, line 5, delete "represents" (second occurrence).

UNITED STATES PATENT AND TRADEMARK OFFICE
CERTIFICATE OF CORRECTION

PATENT NO. : 5,750,738
DATED : May 12, 1998
INVENTOR(S) : Jean-Pierre Bastart et al.

It is certified that error appears in the above-identified patent and that said Letters Patent is hereby corrected as shown below:

Claim 1, column 7, line 7, "2 t o 8" should read --2 to 8--.

Claim 1, column 7, line 25, "atoms," should read --atoms),--.

Claim 1, column 8, line 4 delete "a" (second occurrence).

Claim 1, column 8, line 21, "in" should read --is--.

Claim 2, column 8, line 24, "basic-organic" should read --basic organic--.

Signed and Sealed this

Eighth Day of June, 1999

Attest:

Q. TODD DICKINSON

*Attesting Officer*     *Acting Commissioner of Patents and Trademarks*